US011419885B2

(12) United States Patent
Sprenger et al.

(10) Patent No.: US 11,419,885 B2
(45) Date of Patent: *Aug. 23, 2022

(54) COMPOSITIONS FOR USE IN THE PREVENTION OR TREATMENT OF URT INFECTIONS IN INFANTS OR YOUNG CHILDREN AT RISK

(71) Applicant: NESTEC S.A., Vevey (CH)

(72) Inventors: Norbert Sprenger, Savigny (CH); Clemens Kunz, Wettenberg (DE); Dominique Brassart, Chavannes-pres-renens (CH)

(73) Assignee: Societe des Produits Nestle S.A., Vevey (CH)

(*) Notice: Subject to any disclaimer, the term of this patent is extended or adjusted under 35 U.S.C. 154(b) by 388 days.

This patent is subject to a terminal disclaimer.

(21) Appl. No.: 16/437,454

(22) Filed: Jun. 11, 2019

(65) Prior Publication Data
US 2019/0290668 A1 Sep. 26, 2019

Related U.S. Application Data

(63) Continuation of application No. 15/036,863, filed as application No. PCT/EP2014/074555 on Nov. 14, 2014, now Pat. No. 10,357,506.

(30) Foreign Application Priority Data

Nov. 15, 2013 (EP) .................................. 13193087

(51) Int. Cl.
A61K 31/702 (2006.01)
A61K 45/06 (2006.01)
A61K 35/741 (2015.01)
A23L 33/00 (2016.01)
A61K 9/00 (2006.01)
A61K 35/00 (2006.01)

(52) U.S. Cl.
CPC ............ A61K 31/702 (2013.01); A23L 33/40 (2016.08); A61K 9/0053 (2013.01); A61K 35/741 (2013.01); A61K 45/06 (2013.01); A23V 2002/00 (2013.01); A61K 2035/115 (2013.01)

(58) Field of Classification Search
CPC ............. A61K 2300/00; A61K 31/702; A61K 35/741; A61K 2035/115; A61K 45/06; A61K 9/0053; A23V 2200/314; A23V 2250/28; A23L 33/40
See application file for complete search history.

(56) References Cited

U.S. PATENT DOCUMENTS 5,288,637 A 2/1994 Roth
9,943,556 B2* 4/2018 Sprenger ............... A23L 33/135
10,357,506 B2* 7/2019 Sprenger ............... A61K 31/702
2004/0058418 A1 3/2004 Endo et al.
2010/0260720 A1 10/2010 Sprenger
2011/0020304 A1* 1/2011 Sprenger ................ A61P 1/00 424/93.45
2012/0114608 A1 5/2012 Ebel et al.
2012/0315250 A1 12/2012 Wacklin et al.
2013/0236424 A1 9/2013 Sprenger

FOREIGN PATENT DOCUMENTS

| CN | 101432007 A | 5/2009 | |
|---|---|---|---|
| EP | 0975235 | 2/2000 | |
| WO | 9610086 A1 | 4/1996 | |
| WO | 9843494 A1 | 10/1998 | |
| WO | 2005055944 A2 | 6/2005 | |
| WO | 2006007526 A1 | 1/2006 | |
| WO | 2006022542 A1 | 3/2006 | |
| WO | 2007046697 A1 | 4/2007 | |
| WO | WO-2007101675 A1 * | 9/2007 | ........... A23C 9/1425 |
| WO | 2008042101 A2 | 4/2008 | |
| WO | 2009077352 A1 | 6/2009 | |
| WO | 2009112361 A2 | 9/2009 | |
| WO | 2009151315 A1 | 12/2009 | |
| WO | 2009151330 | 12/2009 | |
| WO | 2010002241 A1 | 1/2010 | |
| WO | 2011008086 A1 | 1/2011 | |
| WO | WO-2011008087 A1 * | 1/2011 | ............. A23L 29/30 |
| WO | 2011080396 A2 | 7/2011 | |
| WO | 2011136648 A1 | 11/2011 | |
| WO | 2012062780 A1 | 5/2012 | |
| WO | 2012092154 A1 | 7/2012 | |
| WO | 2012092159 A1 | 7/2012 | |

OTHER PUBLICATIONS

Gibson et al., "Dietary modulation of the human colonic microbiota: introducing the concept of prebiotics", Journal of nutrition, Jun. 1995, vol. 125(6), pp. 1401-1412.
Salminen et al., "Probiotics: how should they be defined?", Trends in Food Science & Technology, Mar. 3, 1999, vol. 10, No. 3, pp. 107-110.
Bespalov et al., "Biologically active dietary supplements and possibilities of their use in preventive medicine", 2001, pp. 196.
Wrodnigg et al., "The Heyns Rearrangement Revisited: An Exceptionally Simple Two-Step Chemical Synthesis of D-Lactosamine from Lactulose", Angew Chem Int Ed Engl.,Mar. 15, 1999, vol. 38(6), pp. 827-828.

(Continued)

Primary Examiner — Susan M Hanley
(74) Attorney, Agent, or Firm — K&L Gates LLP

(57) ABSTRACT

A composition contains at least one fucosylated oligosaccharide, for use in preventing and/or treating a URT infection in an infant or young child fulfilling at least one of the following criteria: i) the infant or young child is born from a non-secretor mother and/or is fed with a mother's milk deficient in at least one fucosylated oligosaccharide, ii) the infant or young child has at least one sibling, and iii) the infant or young child was born by C-section.

16 Claims, 1 Drawing Sheet

(56) References Cited

OTHER PUBLICATIONS

Russia Patent Office Communication for Application No. 2016123516/04(036798) dated Dec. 18, 2018, 9 pages.
Zhang et al., "Guidelines for Parenting of Infants or Young Children", China Women Publishing House, 1st edition, Jun. 2006, p. 45.
Chinese Patent Office Communication for corresponding application No. 201480062155.6, dated Feb. 1, 2019, 7 pages.
Population statistics of children in the US from Childstats.gov downloaded from http://www.childstats.gov/AMERICACHILDREN/tables/pop 1.aspon Jun. 25, 2018 (Year: 2018).
Rubaltelli et al. Biol. Neonate (1998) 74: 7-15.
Definition of FUT2 downloaded from http://medical-dictionary.thefreedictioniary/com/FUT2 on Sep. 27, 2017.
Idanpaan-Heikkila et al., "Oligosaccharides Interfere with the Establishment and Progresssion of Experimental Pneumococcal Pneumonia", The Journal of Infectious Diseases, vol. 176, Issue No. 3, 1997, pp. 704-712.
Weichert et al., "Bioengineered 2'-Fucosyllactose and 3-Fucosyllactose Inhibit the Adhesion of Pseudomonas Aeruginosa and Enteric Pathogens to Human Intestinal and Respiratory Cell Lines", Nutrition Research, vol. 33, Issue No. 10, 2013, pp. 831-838.
Thomas et al., "Common Oligosaccharide Moieties Inhibit the Adherence of Typical and Atypical Respiratory Pathogens", Journal of Medical Microbiology, vol. 53, Issue No. 9, 2004, pp. 833-840.
Tong et al., "Effect of Lacto-N-Neotefraose,Asialoganglioside-GM1 and Neuraminidase on Adherence of Otitis Media-Associated Serotypes of *Streptococcus pneumoniae* to Chinchilla Tracheal Epithelium", Microbial Pathogenesis, vol. 26, Issue No. 2, 1999, pp. 111-119.
European Patent Office Communication for Application No. 16175652.3-1112 / 3111942, dated Oct. 12, 2021, 16 pages.
Thurl et al., "Variation of Human Milk Oligosaccharides in Relation to Milk Groups and Lactational Periods", British Journal of Nutrition, vol. 104, Issue No. 9, 2010, pp. 1261-1271.
Arslanoglu et al., "Early Dietary Intervention with a Mixture of Prebiotic Oligosaccharides Reduces the Incidence of Allergic Manifestations and Infections during the First Two Years of Life", The Journal of Nutrition, vol. 138, Issue No. 6, 2008, pp. 1091-1095.
European Patent Office Communication for Application No. 14798854.7-1112/ 3068404 dated Oct. 13, 2021, 19 pages.

* cited by examiner

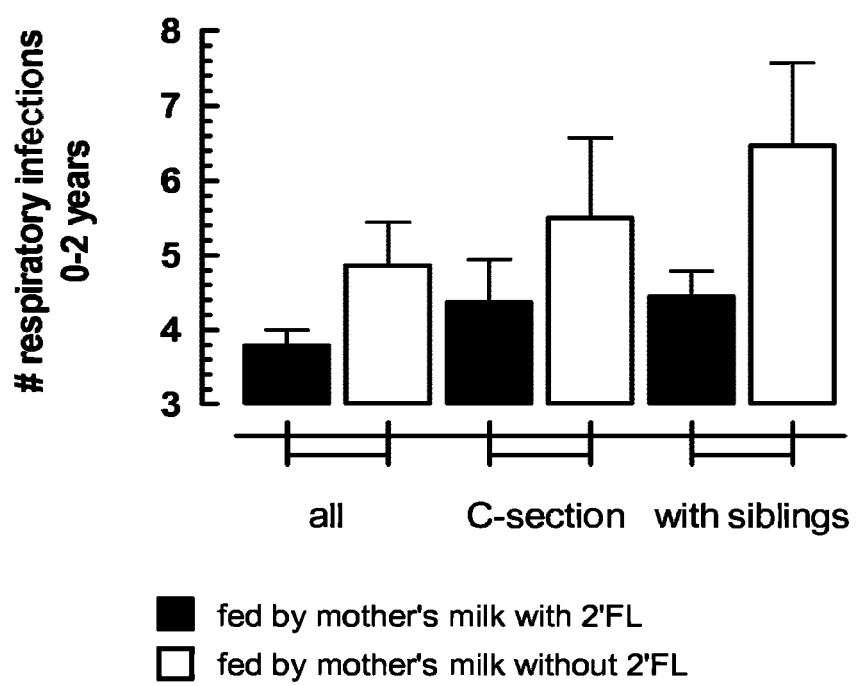

COMPOSITIONS FOR USE IN THE PREVENTION OR TREATMENT OF URT INFECTIONS IN INFANTS OR YOUNG CHILDREN AT RISK

PRIORITY CLAIMS

This application is a continuation of U.S. application Ser. No. 15/036,863 filed May 16, 2016, which is a National Stage of International Application No. PCT/EP14/74555 filed Nov. 14, 2014, which claims priority to European Patent Application No. 13193087.7 filed Nov. 15, 2013, the entire contents of which are incorporated herein by reference.

FIELD OF THE INVENTION

This invention relates to compositions for use in preventing and/or treating upper respiratory tract (URT) infections in infants or young children having high risks of catching infections.

BACKGROUND

Upper respiratory tract infections (also called URT infections or URTI) are illnesses caused by an acute infection involving the upper respiratory tract: nose, sinuses, pharynx and/or larynx. The most common examples of URT infections are rhinitis, rhinosinusitis, nasopharyngitis, haryngitis, epiglottitis, laryngitis, tonsillitis, laryngotracheitis, tracheitis, or combinations thereof.

URTI are often caused by viruses. Over 200 different viruses have been isolated in patients with URIs. The most common virus is called the rhinovirus. Other viruses include the coronavirus, parainfluenza virus, adenovirus, enterovirus, and respiratory syncytial virus.

The most common symptoms of upper respiratory tract infections are cough, sore throat, runny nose, nasal congestion, headache, low grade fever, facial pressure, sneezing, and combinations thereof. URT infections are usually associated with tiredness, discomfort and a loss of performance and concentration.

There can also be some complications associated with URT infections such as ear infection like otitis media and sometimes bronchitis.

All human can have URT infections. In particular children (including young children) are very likely to catch URT infections since they come into close contact with many other individuals, e.g., in school or in kinder garden.

Infants (i.e. babies from birth up to 1 year of age) are also prone to develop URT infections in view of their weak conditions and immature immune defenses. However they will require a special attention since the consequences on their health of such diseases can be serious compared with other individuals.

Many attempts have been made to prevent URT infections. The use of probiotics has especially been investigated. Probiotics are considered to be viable microbial preparations which promote the individual's health by preserving the natural microflora in the intestine. Probiotics are deemed to attach to the intestine's mucosa, colonize the intestinal tract and likewise prevent attachment of harmful microorganisms thereon. A crucial prerequisite for their action resides in that they have to reach the gut's mucosa in a proper and viable form and do not get destroyed in the upper part of the gastrointestinal tract, especially by the influence of the low pH prevailing in the stomach.

For example WO2008042101 from Danisco provides methods for reducing respiratory disease in children, comprising: providing a culture of *L. acidophilus*; providing a child at risk of developing respiratory disease; and administering the culture of *L. acidophilus* to the child at risk, under conditions such that the risk of developing respiratory disease is reduced. However, adding live probiotic bacteria to products so that they remain viable until consumption is a non-trivial task. In particular for products with longer storage times this is difficult to accomplish and may require additional technical efforts. This invention targets young children who are preferably from 3 to 5 years old.

WO2012/062780 from Nestec SA disclosed composition comprising non-replicating probiotic micro-organisms for use in the prevention or treatment of upper respiratory tract infections and/or its symptoms. This composition can offer the probiotic benefits while being easy to prepare and to store without loss of activity.

Other pathways than probiotics have been explored such as the use of oligosaccharides, and especially human milk oligosaccharides. Human milk oligosaccharides (HMOs) are, collectively, the third largest solid constituents in human milk, after lactose and fat. HMOs usually consist of lactose at the reducing end with a carbohydrate core that often contains a fucose or a sialic acid at the non-reducing end.

There are approximately one hundred milk oligosaccharides that have been isolated and characterized in human milk, however this represents only a very small portion of the total number remaining to be characterized. Mother's milk is recommended for all infants. However, in some cases breast feeding is inadequate or unsuccessful for medical reasons or the mother chooses not to breast feed. Infant formulae have been developed for these situations. Fortifiers have also been developed to enrich mother's milk or infant formula with specific ingredients.

Several compositions have therefore been developed using HMO ingredients, such as fucosylated oligosaccharides, lacto-N-tetraose, lacto-N-neotetraose or sialylated oligosaccharides, and for different purposes.

For example WO2005055944 from Children's hospital medical center describes a pharmaceutical composition comprising a molecule comprising a fucose group in an alpha-2 linkage, an alpha-3 linkage or an alpha-4 linkage to a galactose group and a pharmaceutically acceptable carrier. Various molecules are described such as 2'-fucosyllactose. This application is quite general since several infections can be prevented or treated, including respiratory or enteric infections, and there is a large target of patients (infants, children or adults).

Further studies were specifically focused on various associations of HMOs with either a probiotic strain or with other specific components.

For example WO2009/077352 from Nestec SA relates to a composition suitable in the prevention of opportunistic infections comprising a particular synergistic association of a probiotic *Bifidobacterium* with a fucosylated oligosaccharide. Respiratory tracts infections are cited amongst the opportunistic infections that may be prevented. This invention especially targets immune-compromised individuals such as preterm infants, older children or adults with an immune system which is not fully effective as a result of an existing condition or illness (e.g. HIV) or as a result of therapy for an existing condition e.g. Crohn's disease or rheumatoid arthritis or chemo-therapy for the treatment of cancer).

WO2009/112361 from Nestec SA relates to another composition suitable in the prevention of opportunistic infections comprising a particular synergistic association of a N-acetyl-lactosamine and/or an oligosaccharide containing N-acetyl-lactosamine with a probiotic *Lactobacillus* sp. Several conditions are cited such as pathogenic infections of the upper respiratory tract.

WO2012/092154 from Abbott refers to methods of using HMOs for improving airway respiratory health of infants, toddlers and children. However a wide list of HMOs is indicated in this application as well as several combinations of different HMOs. It is claimed that the composition seems to be efficient when HMOs are present with carotenoid.

WO2011/136648 from Nutricia is focused on the use of a composition comprising HMOs such as 2-fucosylated oligosaccharides for the preparation of a nutritional composition for feeding an infant, said infant having Lewis blood type Le(a−/b+) or Le(a−/b−) and/or Lewis blood type Le(x−/y+) or Le(x−/y−). However this application does not refer to the prevention and/or treatment of URT infections.

None of the previous work is therefore focused on the prevention and/or treatment of URT infections in infants or young children having higher risks of infections than the average, especially higher risks of catching URT infections. These infants and these young children represent a subgroup of subjects of a higher concern and who require a higher care than the other infants or young children since they will be more prone to get such diseases and the associated complications.

There is therefore a need for these infants at risk or these young children at risk to develop an efficient specific composition that will allow preventing and/or treating the URT infections.

There is also a need to deliver such health benefits in a manner that is particularly suitable for these young subjects (infants and young children), in a manner that does not involve a classical pharmaceutical intervention as these infants or young children are particularly fragile.

There is a need to deliver such health benefits in at risk subjects in a manner that does not induce side effects and/or in a manner that is easy to deliver, and well accepted by the parents or health care practitioners.

There is also a need to deliver such benefits in a manner that does keep the cost of such delivery reasonable and affordable by most.

Overall there is a need to deliver the most appropriate positive health effects to the specific sub-populations in needs, without unnecessarily targeting broad and large populations.

SUMMARY

The present inventors were able to identify infants or young children having higher risks to catch URT infections. Such infant or young child at risk fulfils at least one of the following criteria:
i) the infant or young child is born from a non-secretor mother and/or is fed with a mother's milk that is deficient in at least one fucosylated oligosaccharide(s)
ii) the infant or young child has at least one sibling
iii) the infant or young child was born by C-section The present inventors have found that a composition comprising at least one fucosylated oligosaccharide can advantageously be used against URT infections in said infants at risk or in said young children at risk.

Accordingly, the present invention provides a composition comprising at least one fucosylated oligosaccharide, for use in preventing and/or treating URT infections in particular sub-populations of infants and young children, especially in an infant or young child fulfilling at least one of the following criteria:
i) the infant or young child is born from a non-secretor mother and/or is fed with a mother's milk deficient in at least one fucosylated oligosaccharide(s)
ii) the infant or young child has at least one sibling
iii) the infant or young child was born by C-section

FIGURES

FIG. 1 represents the number of respiratory infections up to 2 years of age against all infants, infants born by C-section and infants with at least one sibling at birth (x-axis). Groups are separated into those who consumed milk with 2'FL and those who consumed 2'FL deficient milk from their mothers in the first months of life. (Mean with SEM; significance tested by ANOVA)

DETAILED DESCRIPTION

As used herein, the following terms have the following meanings.

The term "infant" means a child under the age of 12 months.

The expression "young child" means a child aged between one and three years, also called toddler.

An "infant or young child born by C-section" means an infant or young child who was delivered by caesarean. It means that the infant or young child was not vaginally delivered.

A "preterm" or "premature" means an infant or young child who was not born at term. Generally it refers to an infant or young child born prior 36 weeks of gestation.

The expression "nutritional composition" means a composition which nourishes a subject. This nutritional composition is usually to be taken orally or intravenously, and it usually includes a lipid or fat source and a protein source.

The expression "hypoallergenic nutritional composition" means a nutritional composition which is unlikely to cause allergic reactions.

In a particular embodiment the composition of the present invention is a "synthetic composition". The expression "synthetic composition" means a mixture obtained by chemical and/or biological means, which can be chemically identical to the mixture naturally occurring in mammalian milks (i.e. the synthetic composition is not breast milk).

The expression "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The expression "starter infant formula" means a foodstuff intended for particular nutritional use by infants during the first four months of life.

The expression "follow-on formula" means a foodstuff intended for particular nutritional use by infants aged over four months or by young children and constituting the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "fortifier" refers to liquid or solid nutritional compositions suitable for mixing with breast milk or infant formula.

The term "weaning period" means the period during which the mother's milk is substituted by other food in the diet of an infant or young child.

The expressions "URT infections", "Upper respiratory tract infections" and "URTI" can be used interchangeably. The most common examples of URT infections are rhinitis, rhinosinusitis, nasopharyngitis, pharyngitis, epiglottitis, laryngitis, tonsillitis, laryngotracheitis, tracheitis, or combinations thereof.

The expressions "to prevent URT infections", "preventing URT infections" or "prevention of URT infections" mean avoiding that URT infections occur and/or decreasing the incidence of the URT infections (reduction of the frequency, i.e. the number of URT infections). In some embodiments the prevention of URT infections is during the treatment (i.e. during the administration of the composition of the present invention). It can also encompass the prevention of URT infections later in life. The term "later in life" encompasses the effect after the termination of the intervention or treatment. The effect "later in life" can be from 1 week to several months, for example from 2 to 4 weeks, from 2 to 6 weeks, from 2 to 8 weeks, from 1 to 6 months or from 2 to 12 months.

The expressions "to treat URT infections", "treating URT infections" or "treatment of URT infections" should be understood as comprising the decrease of the duration of the URT infections (number of days/weeks/years the infants or young children will suffer from URT infections), of the severity of URT infections (the consequences and/or the seriousness of URT infections). These expressions also encompass the relieve of the symptoms such as cough, sore throat, runny nose, nasal congestion, headache, low grade fever, facial pressure, sneezing, and combinations thereof, and/or the decrease of complications caused by URT infections on the infant or young child health, such as otitis media and sometimes bronchitis, and/or the decrease of pain, and/or the decrease of tiredness, and/or the ease of the sleep and/or the stabilization of the activity of the infants or young children suffering from URT infections.

The "mother's milk" should be understood as the breast milk or the colostrum of the mother.

In the present invention the "infant(s) at risk" or the "young child/children at risk" represent infant(s) or young child/children having higher risks of infections than usual (i.e. than the average), especially higher risks of catching URT infections, for example during the first month, 3 months, 6 months, 1 year, 2 years or 5 years of life, or even longer. This means that if we look at these infants or young children, there will be a higher incidence of URT infections in these infants or young children, and/or higher duration of the URT infections in these infants or young children, and/or a higher severity of URT infections in these infants or young children, and/or a longer time to relieve the symptoms of the URT infections in these infants or young children, in comparison with other infants or young children of the same age (i.e. who are not at risks that is to say who do not fulfils a least one of the criteria i), ii), iii)).

The infant or young child at risk according to the invention is an infant or a young child fulfilling at least one of the following criteria:

i) the infant or young child is born from a non-secretor mother and/or is fed with a mother's milk deficient in at least one fucosylated oligosaccharide(s)

ii) the infant or young child has at least one sibling iii) the infant or young child was born by C-section Concerning criteria i), by the expression "deficient in at least one fucosylated oligosaccharide(s)", it is meant a mother's milk that lacks, is depleted of or is poor in fucosylated oligosaccharides (or at least one of them) and especially in fucosylated oligosaccharides comprising a 2' fucosyl-epitope (also called 2-fucosylated oligosaccharides), e.g. 2FL. The milk may contain no (or almost no) fucosylated oligosaccharides, or a low amount of fucosylated oligosaccharides such as an amount which represent less than 50%, or less than 40%, or less than 35%, or less than 30%, or less than 25%, or less than 20%, or less than 15%, or less than 10%, or less than 5%, or less than 3%, or less than 2% of the mean (or average) amount that is generally found in the breast mother's milk.

Such expression is generally recognized by the absence or presence at low levels of said fucosylated oligosaccharides in the mother's milk. Alternatively such expression is recognized by genetic analysis or measurements in other body fluids.

In one embodiment the mother's milk is fully depleted in at least one fucosylated oligosaccharides, such as in oligosaccharides comprising a 2'-fucosyl-epitope (also called 2-fucosylated oligosaccharides), e.g. in 2FL. The expression "fully depleted" means that the level of these oligosaccharides is not detectable by usual analytical methods.

In one embodiment the mother's milk fed to the infant or young child is depleted in at least one fucosylated oligosaccharide(s) in the sense that it has a concentration of said fucosylated oligosaccharide(s) (such as oligosaccharides comprising a 2'-fucosyl-epitope, e.g. 2FL) of less than 3000 mg/L, less than 2000 g/L, less than 1000 mg/l, less than 500 mg/L, less than 300 mg/L, less than 100 mg/L, less than 50 mg/L, less than 10 mg/L, 1 mg/L.

In one embodiment the infant or young child is actually fed or partially fed, or temporarily fed with the mother's milk that is deficient in at least one fucosylated oligosaccharide(s).

In particular embodiments the infant or young child is "born from a non-secretor mother". In some embodiments the infant or young child is "breastfed with a mother's milk from a non-secretor mother". A non-secretor mother will produce or at least will have higher chances to produce breast milk that is deficient in at least one fucosylated oligosaccharide(s). Genetic variants of specific glycosyltransferases are well known to affect very specific milk prebiotic components and glycan structures. The basis for the phenotypic difference between the secretor and non-secretor subpopulations stems from genetic polymorphisms resulting in the expression of a specific functional alpha-1,2-fucosyltransferase (also called fucosyltransferase-2 or Fut2) in case of secretors whereas non-secretors do not express this functional alpha-1,2-fucosyltransferase. Accordingly, mutations in this gene lead to deficient amounts of 2'fucosyl-glycans (oligosaccharides) secreted into biological fluids (such as milk) of non-secretors people. The secretor (sec+) and non-secretor (sec−) status of a person can be determined using the Lewis blood typing system, commonly known by a skilled man and also explained in WO2011136648.

The terms "sec+" and "sec$^+$" can be used interchangeably. The terms "sec−" and "sec$^-$" can be used interchangeably.

Concerning criteria ii), the sibling can be a brother or a sister who can be younger or older than the infant or young child at risk. In some embodiments the infant or young child has at least one sibling who is older than him i.e. the infant or young child has at least one sibling at birth. It may especially be a child (including young child) who is very likely to catch URT infections since he comes into close contact with many other individuals, e.g., in school or in kinder garden.

Concerning criteria iii), it should be emphasized that infants or young children born by C-section have particular needs due to their particular physiological conditions and there is a high risk that these infants or young children are exposed to diseases such as URT infections, for example due to the fact that their microbiota is not properly developed or not adapted. Indeed immediately before birth, the gastrointestinal tract of a baby is thought to be sterile. During the normal process of birth via the vaginal delivery, it encounters bacteria from the urogenital and digestive tracts, the skin and the environment of the mother and starts to become colonized. Infants or young children born from C-section therefore do not encounter these bacteria during birth.

These above-mentioned infants or young children at risk represent a sub-group of subjects of a higher concern and who require a higher care than the other infants or young children since they will be more prone to get URT infections and the associated complications.

It is therefore thought that the administration of at least one fucosylated oligosaccharide—an oligosaccharide already described for the use of infections such as URT infections—to these infants or young children will be particularly efficient on these infants or young children at risk, since, without wishing to be bound by theory, it is believed that:

When an infant or a young child is born from a non-secretor mother and/or fed with a mother's milk deficient in at least one fucosylated oligosaccharide(s), it is hypothesized that such subjects would not be exposed and/or would not get the necessary amount of fucosylated oligosaccharide(s), especially 2-FL. Indeed the mother will not be able to pass to the subject such necessary quantity of fucosylated oligosaccharide(s). The right amount of necessary of fucosylated oligosaccharide(s), in particular 2FL is hypothesized to provide a protection against URT. Therefore the administration or supplementation of such oligosaccharides should be effective to said infants or young children to prevent/treat the URT infections.

When an infant or a young child has at least one sibling, he will have more risks to catch infections such as URT infections because of his sibling, and therefore the administration or supplementation of at least one fucosylated oligosaccharide(s) should allow to help preventing and/or treating URT infections on said infants or young children.

When an infant or a young child is born by C-section, its microbiota is not properly developed or not adapted and therefore he will have more risks to catch infections such as URT infections. The administration or supplementation of at least one fucosylated oligosaccharide(s) should allow to help preventing and/or treating URT infections on said infants or young children either because the fucosylated oligosaccharide(s) may act as competitor for the pathogens and/or as a favorable angiogenesis agent allowing maturation of the immune system and/or it will allow developing a proper microbiota on said infants or young children.

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

A "fucosylated oligosaccharide" is an oligosaccharide having a fucose residue. It has a neutral nature. Some examples are 2-FL (2'-fucosyllactose), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyl-lacto-N-neohexaose, difucosyllacto-N-hexaose I, difucosyl-lacto-N-neohexaose II and any combination thereof. Without wishing to be bound by theory it is believed that the fucosyl-epitope of the fucosylated oligosaccharides may act as decoy at the mucosal surface. By a competition effect, it may prevent and/or limit the action of the pathogens responsible of infections (of viral or bacterial origin) or of their secreted components (e.g. toxins), especially by avoiding their binding to natural ligands, and this will therefore reduce the risk of infections, and particularly of URT infections.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected.

Without wishing to be bound by theory, the 2' fucosyl-epitope of these fucosylated oligosaccharides is believed to be particularly specific to pathogens (or their secreted components) involved in URT infections.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose) and LNnT (lacto-N-neotetraose).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. Dietary modulation of the human colonic microbiota: introducing the concept of prebiotics. *J Nutr.* 1995; 125:1401-12).

The term "probiotic" means microbial cell preparations or components of microbial cells with a beneficial effect on the health or well-being of the host. (Salminen S, Ouwehand A. Benno Y. et al. "Probiotics: how should they be defined"

Trends Food Sci. Technol. 1999:10 107-10). The microbial cells are generally bacteria or yeasts.

The term "cfu" should be understood as colony-forming unit.

All percentages are by weight unless otherwise stated.

The invention will now be described in further details. It is noted that the various aspects, features, examples and embodiments described in the present application may be compatible and/or combined together.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

A first object of the present invention is therefore a composition comprising at least one fucosylated oligosaccharide, for use (or suitable for use) in preventing and/or treating URT infections in an infant or a young child fulfilling at least one of the following criteria:
  i) the infant or young child is born from a non-secretor mother and/or fed with a mother's milk deficient in at least one fucosylated oligosaccharide(s)
  ii) the infant or young child has at least one sibling
  iii) the infant or young child was born by C-section In other words the infant or young child is an infant at risk or a young child at risk who can be born from a non-secretor mother and/or fed with a mother's milk deficient in at least one fucosylated oligosaccharide(s) and/or who can have at least one sibling and/or who can be born by C-section.

As previously explained these infants or young children at risk will be more prone to catch URT infections and the associated complications. It is therefore thought that the administration of at least one fucosylated oligosaccharide to these particular infants or young children will therefore be efficient in the prevention and/or treatment of URT infections, especially for the reasons previously mentioned.

In some embodiments the infant or young child fulfils one, two or three of the criteria i), ii) and iii).

In some embodiments the infant or young child fulfils at least two of the criteria i), ii) and iii).

In some embodiments the invention is about a composition comprising at least one fucosylated oligosaccharide, for use (or suitable for use) in preventing and/or treating URT infections in an infant or a young child fulfilling at least one of the following criteria:
  i) the infant or young child is fed with a mother's milk deficient in at least one fucosylated oligosaccharide(s)
  ii) the infant or young child has at least one sibling
  iii) the infant or young child was born by C-section In some embodiments the infant at risk or young child at risk is an infant or young child fed with a mother's milk deficient in at least one fucosylated oligosaccharide(s) and who has at least one sibling.

In some other embodiments the infant at risk or young child at risk is an infant or young child fed with a mother's milk deficient in at least one fucosylated oligosaccharide(s) and who was born by C-section.

In some other embodiments the infant at risk or young child at risk is an infant or young child who has at least one sibling and who was born by C-section.

In some other embodiments the infant at risk or young child at risk is an infant or young child fed with a mother's milk deficient in at least one fucosylated oligosaccharide(s), has at least one sibling and was born by C-section.

In some particular embodiments the infant or young child has at least one sibling at birth.

In some embodiments the infant or young child is fed with a mother's milk from a non-secretor mother.

The infant or young child can be secretor or non-secretor using the Lewis blood typing system. In a particular embodiment, the infant or young child is secretor. This implies that the infant or young child will express some surface epitopes (analogues) for at least one fucosylated oligosaccharide(s), and especially for at least one fucosylated oligosaccharides comprising a 2'-fucosyl-epitope (also called 2-fucosylated oligosaccharides) such as 2FL.

In a particular embodiment, the infant or young child is secretor using the Lewis blood typing system whereas he was born from a non-secretor mother.

The composition of the present invention comprises at least one fucosylated oligosaccharide. There can be one or several fucosylated oligosaccharide(s). The fucosylated oligosaccharide(s) can be selected from the list comprising 2'-fucosyllactose, 3'fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

Some examples of lacto-N-fucopentaose are lacto-N-fucopentaose I, lacto-N-fucopentaose II, lacto-N-fucopentaose III, lacto-N-fucopentaose V.

In a particular embodiment of the present invention the fucosylated oligosaccharide is 2'-fucosyllactose (2-FL, also abbreviated 2FL, 2'FL, or 2'-FL).

The fucosylated oligosaccharide may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The composition according to the invention can contain from 0.1 to 10 g of fucosylated oligosaccharide(s) per 100 g of composition on a dry weight basis, e.g. from 0.1 to 8 g, or from 0.1 to 4 g, or from 0.5 to 3 g of fucosylated oligosaccharide(s) per 100 g of composition on a dry weight basis.

In particular examples the composition comprises from 0.5 to 10 g/L of fucosylated oligosaccharide(s), or from 0.5 to 5 g/L, or from 1 to 4.5 g/L, or from 2 to 4 g/L, or from 2.5 to 3.5 g/L of fucosylated oligosaccharide(s). The amount of fucosylated oligosaccharide(s) will be adapted depending on the needs of the infant or young child. In some examples, the composition can comprise from 0.5 to 2 g/L or from 0.7 to 1.8 g/L of fucosylated oligosaccharide(s). In some other examples, the composition can comprise higher levels of fucosylated oligosaccharide(s) such as from 5 to 10 g/L or from 6 to 8 g/L of fucosylated oligosaccharide(s), such as 2FL.

The composition according to the invention can comprise at least another human milk oligosaccharide(s) and/or precursor(s) thereof. There can be one or several other human milk oligosaccharide(s) and/or precursor(s) thereof, for example 1, 2, 3, 4, 5 or even more HMO(s) (and/or precursor(s) thereof) other than the at least one fucosylated oligosaccharide(s).

These other human milk oligosaccharide(s) and/or precursor(s) thereof may be selected from the list comprising N-acetylated oligosaccharide, sialylated oligosaccharide, sialic acid, fucose and any combination thereof.

Therefore the composition according to the invention can also comprise N-acetylated oligosaccharide(s). There can be one or several N-acetylated oligosaccharide(s). The N-acetylated oligosaccharide(s) can be selected from the group comprising lacto-N-tetraose (LNT), lacto-N-neotetraose (LNnT) and any combination thereof.

In some particular embodiments the N-acetylated oligosaccharide is LNT.

In some particular embodiments the N-acetylated oligosaccharide is LNnT.

In some particular embodiments the N-acetylated oligosaccharide is a mixture of LNT and LNnT.

In some particular embodiments the composition comprises both LNT and LNnT in a ratio LNT:LNnT between 5:1 and 1:2, or from 2:1 to 1:1, or from 2:1.2 to 2:1.6.

LNT and LNnT may be synthesized chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

The composition according to the invention can contain from 0.1 to 5 g of N-acetylated oligosaccharide(s)/100 g composition on a dry weight basis or from 0.1 to 3 g of N-acetylated oligosaccharide(s)/100 g composition on a dry weight basis.

In particular examples the composition comprises LNT in an amount of from 0.1 to 4, or from 0.3 to 3 or from 0.4 to 2 or from 0.4 to 1, or from 0.4 to 0.9 g/L of composition.

In particular examples the composition comprises LNnT in an amount of from 0.1 to 4, or from 0.2 to 2 or from 0.3 to 1.5 or from 0.4 to 1, or from 0.4 to 0.9 g/L of composition. In some embodiments, the composition comprises both LNT and LNnT in these above-mentioned concentrations.

The composition according to the invention can comprise sialylated oligosaccharide(s). There can be one or several sialylated oligosaccharide(s).

The sialylated oligosaccharide(s) can be selected from the group comprising 3' sialyllactose (3-SL), 6' sialyllactose (6-SL), and any combination thereof.

In some embodiments of the invention the composition comprises 3-SL and 6-SL.

In some particular embodiments the ratio between 3'-sialyllactose (3-SL) and 6'-sialyllactose (6-SL) can be in the range between 5:1 and 1:10, or from 3:1 and 1:1, or from 1:1 to 1:10.

In some specific embodiments the sialylated oligosaccharide of the composition is 6' sialyllactose (6-SL).

The 3'- and 6'-forms of sialyllactose may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerization (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

The composition according to the invention can contain from 0.05 to 5 g of sialylated oligosaccharide(s) per 100 g of composition on a dry weight basis, e.g. from 0.1 to 2 g or from 0.2 to 1 g of sialylated oligosaccharide(s) per 100 g of composition on a dry weight basis.

In particular examples the composition comprises from 0.05 to 5 g/L of sialylated oligosaccharide(s), or from 0.1 to 4 g/L, or from 0.3 to 2 g/L, or from 0.4 to 1.5 g/L, or from 0.4 to 1 g/L, for example 0.5 or 0.9 g/L of sialylated oligosaccharide(s).

In some particular embodiments the composition can comprise from 0.8 to 1.7 g/l of sialylated oligosaccharide(s).

The composition according to the present invention may optionally also comprise at least one precursor of human milk oligosaccharide. There can be one or several precursor(s) of human milk oligosaccharide.

For example the precursor of human milk oligosaccharide is sialic acid, fucose or a mixture thereof.

In some particular embodiments the composition comprises sialic acid.

The composition according to the invention can contain from 0 to 2.3 g of precursor(s) of human milk oligosaccharide per 100 g of composition on a dry weight basis, e.g. from 0 to 1.5 g or from 0 to 0.8 g of precursor(s) of human milk oligosaccharide per 100 g of composition on a dry weight basis.

In particular examples the composition comprises from 0 to 3 g/L of precursor(s) of human milk oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of human milk oligosaccharide.

In some particular embodiments the composition of the present invention therefore comprises at least one fucosylated oligosaccharide in combination with at least another human milk oligosaccharide(s) and/or precursor(s) thereof selected from the list comprising lacto-N-tetraose (LNT), lacto-N-neotetraose (LNnT), 3' sialyllactose (3-SL), 6' sialyllactose (6-SL), sialic acid and any combination thereof.

The composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BLIS Technologies Limited of New Zealand under the designation KI2, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The composition according to the invention typically contains from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The composition of the invention can further comprise at least one non-digestible oligosaccharide (e.g. prebiotics) other than the human milk oligosaccharides previously mentioned. They are usually in an amount between 0.3 and 10% by weight of composition.

Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such a fructooligosaccharides (FOS) and galactooligosaccharides (GOS). A combination of prebiotics may be used such as 90% GOS with 10% short chain fructo-oligosaccharides such as in the product by BENEO-Orafti sold under the trademark Orafti® oligofructose (previously Raftilose®) or 10% inulin such as in the product sold by BENEO-Orafti under the trademark Orafti® inulin (previously Raftiline®). A particularly preferred combination of prebiotics is 70% short chain fructo-oligosaccharides and 30% inulin, which is a product sold by BENEO-Orafti under the trademark "Prebio 1".

The composition of the invention can further comprise at least one phage (bacteriophage) or a mixture of phages, preferably directed against pathogenic Streptococci, *Haemophilus*, *Moraxella* and Staphylococci.

The composition according to the invention can be a nutritional composition, a preparation or a food product.

The composition according to the invention can be for example a nutritional composition such as a synthetic nutritional composition. It can be an infant formula, a starter infant formula, a follow-on formula, a baby food, an infant cereal composition, a fortifier such as a human milk fortifier, or a supplement. In some particular embodiments, the composition of the invention is an infant formula, or a fortifier or a supplement intended for the first 4 or 6 months of age.

In some other embodiments the composition of the present invention is a fortifier.

The fortifier can be a breast milk fortifier or a formula fortifier such as an infant formula fortifier. The fortifier is therefore a particularly advantageous embodiment when the infant or young child fulfils the criteria i) and particularly when the infant or young child is fed with a mother's milk deficient in at least one fucosylated oligosaccharide(s), e.g. a breast mother's milk from a non-secretor mother. Indeed, in an advantageous embodiment, the composition is a human milk fortifier especially designed for non-secretor mothers or other mothers whose milk has low amounts of at least one fucosylated oligosaccharide(s) such as 2'fucosylated oligosaccharide(s).

In some embodiments the composition of the present invention is an infant formula. The infant formula is a particularly advantageous embodiment when the infant fulfils the criteria ii) the infant has at least one sibling and/or iii) the infant was born by C-section.

When the composition is a supplement, it can be provided in the form of unit doses.

The composition of the present invention is typically used in an infant at risk or a young child at risks for use in preventing and/or treating URT infections, i.e. in an infant or a young child fulfilling at least one of the following criteria:

i) the infant or the young child is born from a non-secretor mother and/or fed with a mother's milk deficient in at least one fucosylated oligosaccharide(s), e.g. a breast mother's milk from a non-secretor mother ii) the infant or the young child has at least one sibling iii) the infant or the young child was born by C-section The composition according to the invention can be used in infants or young children at risk that are term or preterm.

In a particular embodiment the composition of the invention is for use in infants or young children at risk that are also preterm.

In some embodiments the composition according to the invention can be for use before and/or during the weaning period.

When there are several oligosaccharide(s) (i.e. either several fucosylated oligosaccharides or one fucosylated oligosaccharide with at least another human milk oligosaccharide(s) and/or the precursor(s) thereof), they may be administered in the same composition or they may be administered sequentially.

The composition of the present invention can be in solid (e.g. powder), liquid or gelatinous form.

For example, when the infant at risk is an infant born by C-section, the composition could advantageously be a nutritional composition consumed in liquid form. In this case it may be a nutritionally complete formula such as an infant formula, a starter formula, a follow-on formula or a fortifier such as a human milk fortifier.

The composition according to the invention generally contains a protein source. The protein can be in an amount of from 1.6 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolyzed or a mixture of intact and hydrolyzed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolyzed" means in the context of the present invention a protein which has been hydrolyzed or broken down into its component amino acids.

The proteins may be either fully or partially hydrolyzed. It may be desirable to supply partially hydrolyzed proteins (degree of hydrolysis between 2 and 20%), for example for infants or young children believed to be at risk of developing cow's milk allergy. If hydrolyzed proteins are required, the hydrolysis process may be carried out as desired and as is known in the art. For example, whey protein hydrolysates may be prepared by enzymatically hydrolyzing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolyzed, preferably at least 80% of the proteins are hydrolyzed, such as at least 85% of the proteins are hydrolyzed, even more preferably at least 90% of the proteins are hydrolyzed, such as at least 95% of the proteins are hydrolyzed, particularly at least 98% of the proteins are hydrolyzed. In a particular embodiment, 100% of the proteins are hydrolyzed.

In one particular embodiment the proteins of the composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the composition according to the invention is a hypoallergenic composition. In another particular embodiment the composition according to the invention is a hypoallergenic nutritional composition.

The composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the composition of the invention may contain emulsifiers and stabilizers such as soy, lecithin, citric acid esters of mono- and diglycerides, and the like.

The composition of the invention may also contain other substances which may have a beneficial effect such as lactoferrin, nucleotides, nucleosides, and the like.

The composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) (and the optional other human milk oligosaccharide(s) and/or the precursor(s) thereof) may be added at this stage, especially if the final product is to have a liquid form.

If the final product is to be a powder, they may likewise be added at this stage if desired.

The liquid mixture is then homogenized, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenized, for example in two stages between about 10 MPa and about 30 MPa in the first stage and between about 2 MPa and about 10 MPa in the second stage. The homogenized mixture may then be further cooled to add any heat sensitive components, such as vitamins and minerals. The pH and solids content of the homogenized mixture are conveniently adjusted at this point.

If the final product is to be a powder, the homogenized mixture is transferred to a suitable drying apparatus such as a spray dryer or freeze dryer and converted to powder. The powder should have a moisture content of less than about 5% by weight. The fucosylated oligosaccharide(s) (and the optional other human milk oligosaccharide(s) and/or the precursor(s) thereof) may be added at this stage by dry-mixing or by blending them in a syrup form of crystals, along with the probiotic strain(s) (if used), and the mixture is spray-dried or freeze-dried.

If a liquid composition is preferred, the homogenized mixture may be sterilized then aseptically filled into suitable containers or may be first filled into the containers and then retorted.

In another embodiment, the composition of the invention may be a supplement including fucosylated oligosaccharide(s) (and the optional other human milk oligosaccharide(s) and/or the precursor(s) thereof) in an amount sufficient to achieve the desired effect in an individual.

The daily dose of the fucosylated oligosaccharide(s) is typically from 0.1 to 4 g, the daily dose of N-acetylated oligosaccharide(s) is typically from 0.1 to 3 g, the daily dose of the sialylated oligosaccharide(s) is typically from 0.1 to 2 g.

The amount of oligosaccharides to be included in the supplement will be selected according to the manner in which the supplement is to be administered. For example, if the supplement is to be administered twice a day, each supplement may contain from 0.05 to 1.5 g of N-acetylated oligosaccharide(s), from 0.05 to 1 g of sialylated oligosaccharide(s), and from 0.05 to 2 g of fucosylated oligosaccharide(s).

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The composition can be administered (or given) at an age and for a period that depends on the needs. The composition is for use in preventing and/or treating URT infections.

In some embodiments the composition is used for the prevention of URT infections. For example the composition can be given immediately after birth of the infants at risk. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some other embodiments, the composition of the invention is given few days, or few weeks, or few months after birth. This may be especially the case when the infant at risk is premature, but not necessarily.

In one embodiment the composition of the invention is given to the infant or young child as a supplementary composition to the mother's milk. In one embodiment the composition is given to the infant or young child as the sole or primary nutritional composition during at least one period of time, e.g. after the $1^{st}$, $2^{nd}$, or $4^{th}$ month, during at least 1, 2, 4 or 6 months. In some embodiments the infant or young child receives the mother's milk during at least the first 2 weeks, first 1, 2, 4, or 6 months. In one embodiment the composition of the invention is given to the infant or young child after such period of mother's nutrition, or is given together with such period of mother's milk nutrition.

In one embodiment the subject is fed only during the first week, the first 2, 4 weeks, or the first 2 or 4 months with milk deficient in at least one fucosylated oligosaccharide(s).

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or follow-on formula.

In some other embodiments the composition of the invention is given when the infant or the young child has caught an URT infection. This will more be the case when the composition is used for the treatment of URT infections.

The composition of the invention can be given for some days (1, 2, 3, 4, 5, 6 . . . ), or for some weeks (1, 2, 3, 4, 5, 6, 7, 8 or even more), or for some months (1, 2, 3, 4, 5, 6, 7, 8, 9, 10, 11 or even more), depending on the needs.

Another object of the present invention is the use of at least one fucosylated oligosaccharide in the preparation of a composition to be administered in an infant or a young child fulfilling at least one of the following criteria:

i) the infant or the young child is born from a non-secretor mother and/or is fed with a mother's milk that is deficient in at least one fucosylated oligosaccharide(s)

ii) the infant or the young child has at least one sibling iii) the infant or the young child was born by C-section, for preventing and/or treating URT infections in said infant or young child.

The present invention also relates to a method for preventing and/or treating URT infections in an infant or a young child fulfilling at least one of the following criteria:

i) the infant or the young child is born from a non-secretor mother and/or is fed with a mother's milk that is deficient in at least one fucosylated oligosaccharide(s)

ii) the infant or the young child has at least one sibling iii) the infant or the young child was born by C-section, said method comprising administering to said infant or young child a composition comprising at least one fucosylated oligosaccharide.

The different embodiments, details and examples previously described in the specification can similarly be applied to these uses and methods.

EXAMPLES

The following examples illustrate some specific embodiments of the composition for use according to the present invention. The examples are given solely for the purpose of illustration and are not to be construed as limitations of the present invention, as many variations thereof are possible without departing from the spirit of the invention.

Example 1

An example of the composition of an infant formula according to the present invention is given in the below table 1. This composition is given by way of illustration only.

TABLE 1 an example of the composition of an infant formula according to the present invention

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| 2FL (g) | 0.45 | 3 |

Example 2

The amounts of the oligosaccharides 2FL (2'fucosyllactose) of human milk samples from a cohort of mother-infant pairs were analyzed. These data were correlated to the number of respiratory infections from 0-2 years of age among the infants. In the cohort of 266 infants, 33 infants consumed milk deficient in 2FL and 233 infants consumed milk with 2FL. 147 infants had no siblings at birth and 119 infants had at least one sibling at birth. 51 infants were born by C-section and 215 infants were born by vaginal birth.

Briefly, milk samples were homogenized and diluted in water, generally 1/10 and 1/100. Diluted samples were centrifuged to remove particles and supernatants were analyzed by high performance anion exchange chromatography coupled with a pulsed amperometric detector (HPAEC-PAD, ICS3000, Dionex) using a Carbopac PA1 analytical column for separation of individual oligosaccharides. Quantification was done with authentic oligosaccharide external standard curves. Peak identification was based on co-migration with authentic oligosaccharide standards.

We performed statistical analyses to find possible associations between (i) the milk types (presence or absence of 2FL) that the infants of the cohort consumed and (ii) the risk for respiratory infections up to the age of 2 years.

We observed that infants who had siblings at birth and/or who were breastfed by mother with 2FL deficient milk and/or who are born by C-section had more respiratory infections up to 2 years of age as shown in FIG. 1.

A composition comprising at least one fucosylated oligosaccharide will therefore be efficient for use in preventing and/or treating URT infections in said infants.

The invention is claimed as follows:

1. A method for preventing and/or treating an upper respiratory tract (URT) infection in an infant or young child, the method comprising administering a composition comprising 0.5 g/L to 5 g/L of 2'-fucosyllactose to an infant or young child,
   wherein the infant or young child is fed with a mother's milk deficient in at least one fucosylated oligosaccharide, and the infant or young child has at least one sibling.

2. The method according to claim 1 wherein the composition further comprises at least one additional fucosylated oligosaccharide selected from the group consisting of 3'fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and combinations thereof.

3. The method according to claim 1 wherein the composition is administered to the infant during at least the first week after birth.

4. The method according to claim 1 wherein the 2'-fucosyllactose is the only human milk oligosaccharide in the composition, and the composition does not contain any carotenoid.

5. The method according to claim 1 wherein the 2'-fucosyllactose is 1 g/L to 4.5 g/L of the composition.

6. The method according to claim 1 comprising administering at least another human milk oligosaccharide and/or precursor thereof to the infant or young child.

7. The method according to claim 6 wherein the at least one human milk oligosaccharide and/or precursor thereof is selected from the group consisting of N-acetylated oligosaccharide, sialylated oligosaccharide, sialic acid, fucose and combinations thereof.

8. The method according to claim 7, wherein the N-acetylated oligosaccharide is selected from the group consisting of lacto-N-tetraose (LNT), lacto-N-neotetraose (LNnT) and combinations thereof.

9. The method according to claim 7, wherein the sialylated oligosaccharide is selected from the group consisting of 3' sialyllactose (3-SL), 6' sialyllactose (6-SL), and combinations thereof.

10. The method according to claim 1 comprising administering to the infant or young child at least another human milk oligosaccharide and/or precursor thereof selected from the group consisting of lacto-N-tetraose (LNT), lacto-N-neotetraose (LNnT), 3' sialyllactose (3-SL), 6' sialyllactose (6-SL), sialic acid and combinations thereof.

11. The method according to claim 1, wherein the composition further comprises at least one probiotic in an amount of from $10^3$ to $10^{12}$ cfu/g of said composition (dry weight).

12. The method according to claim 1, wherein the composition is selected from the group consisting of a nutritional composition, a preparation and a food product.

13. The method according to claim 1, wherein the composition is selected from the group consisting of an infant formula, a starter infant formula, a follow-on infant formula, a baby food, an infant cereal composition, a fortifier and a supplement.

14. The method according to claim 1, wherein the infant or young child is preterm.

15. The method according to claim 1, wherein the infant or young child is a secretor.

16. The method according to claim 1, wherein the composition has a LNT:LNnT weight ratio from 2:1 to 1:1, and/or the infant or young child was born by C-section.

* * * * *